(12) United States Patent
Gambogi et al.

(10) Patent No.: US 11,291,613 B2
(45) Date of Patent: Apr. 5, 2022

(54) COATED PARTICLES AND THEIR USES

(71) Applicant: Johnson & Johnson Consumer Inc., Skillman, NJ (US)

(72) Inventors: Robert Gambogi, Hilsborough, NJ (US); Latrisha Petersen, Somerset, NJ (US); Sherket Peterson, Lawrenceville, NJ (US); Andrew Glowacki, Skillman, NJ (US); Meenakshi Patel, Voorhees, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/981,601

(22) Filed: May 16, 2018

(65) Prior Publication Data

US 2019/0083367 A1   Mar. 21, 2019

Related U.S. Application Data

(60) Provisional application No. 62/506,783, filed on May 16, 2017.

(51) Int. Cl.

| | | |
|---|---|---|
| *A61K 8/02* | (2006.01) | |
| *A61Q 11/00* | (2006.01) | |
| *A61K 8/44* | (2006.01) | |
| *A61K 9/51* | (2006.01) | |
| *A61Q 11/02* | (2006.01) | |
| *A61K 8/85* | (2006.01) | |

(52) U.S. Cl.
CPC .............. *A61K 8/0241* (2013.01); *A61K 8/44* (2013.01); *A61K 8/85* (2013.01); *A61K 9/5153* (2013.01); *A61Q 11/00* (2013.01); *A61Q 11/02* (2013.01); *A61K 2800/413* (2013.01); *A61K 2800/5426* (2013.01); *A61K 2800/622* (2013.01); *A61K 2800/624* (2013.01); *A61K 2800/654* (2013.01)

(58) Field of Classification Search
None
See application file for complete search history.

(56) References Cited

U.S. PATENT DOCUMENTS

| | | |
|---|---|---|
| 4,627,977 A | 12/1986 | Gaffar et al. |
| 5,874,068 A | 2/1999 | Engelman et al. |
| 2011/0123462 A1 | 5/2011 | Mordas et al. |
| 2015/0150818 A1* | 6/2015 | Mousa ................. A61K 31/737 424/451 |
| 2016/0145203 A1 | 5/2016 | Gambogi et al. |

FOREIGN PATENT DOCUMENTS

| | | |
|---|---|---|
| CN | 106 890 105 A | 6/2017 |
| EP | 2 308 473 A1 | 4/2011 |
| JP | 2010-275249 A | 12/2010 |
| JP | 2011-111429 A | 6/2011 |
| JP | 2014-062074 A | 4/2014 |
| WO | WO 2009/032404 A1 | 3/2009 |
| WO | WO 2010/059253 A2 | 5/2010 |
| WO | WO2012/013577 * | 2/2012 |
| WO | WO 2014/130994 A1 | 8/2014 |
| WO | WO 2016/077464 A1 | 5/2016 |

OTHER PUBLICATIONS

Wang et al. (AAPS PharmSciTech, vol. 14, No. 2, Jun. 2013).*
Eldin et al. (Arabian Journal of Chemistry, 8:355-365, 2015).*
Gang Wang, et al.: "Intranasal Delivery of Cationic PLGA Nano/Microparticles—Loaded FMDV DNA Vaccine Encoding IL-6 Elicited Protective Immunity against FMDV Challenge," Plos One, vol. 6, No. 11, Nov. 15, 2011 p. e27605 (XP055495806) DOI: 10.1371/journal.pone.0027605.
Chronopoulou Laura et al.: "Chitosan-coated PLGA nanoparticles: A sustained drug release strategy for cell cultures," Colloids and Surfaces. B, Biointerfaces, Elsevier, Amsterdam, NL; vol. 103, Nov. 20, 2012, pp. 310m-317m (XP028971431, ISSN: 0927-77656; DOI: 10.1016/J. Colsurfb.2012.10.063.
Invitation to Pay Additional Fees etc.) (includes search report) PCT/US2018/032928 dated Aug. 22, 2018.
Yue, Isaac C., et al., A novel polymeric chlorhexidine delivery device for the treatment of periodontal disease; Biomaterials, 2004, v. 25, Iss. 17, pp. 3743-3750; (https://doi.org/10.1016/j.biomaterials.2003.09.113).
Chen, Y.W., et al., Controlled-release of tetracycline and lovastatin by poly(D,L-lactide-co-glycolide acid)-chitosan nanoparticles enhances periodontal regeneration in dogs. International Journal of Nanomedicine, 2016, v.2016; Iss. 1., pp. 285-297.

* cited by examiner

*Primary Examiner* — Bong-Sook Baek

(57) ABSTRACT

Provided are coated particles and methods of their use for providing healthcare benefits. More specifically, the present invention provides amino acid and/or polymer-coated particles, or particles coated with other materials, for binding to, or otherwise associating with, surfaces of the oral cavity.

4 Claims, No Drawings

COATED PARTICLES AND THEIR USES

CROSS-REFERENCE TO RELATED APPLICATION

This application claims the benefit of priority to U.S. Provisional Application No. 62/506,783 filed May 16, 2017.

DESCRIPTION OF THE INVENTION

The present invention relates to new coated particles and their uses. More specifically, in certain embodiments, the present invention provides amino acid and/or polymer-coated particles, or particles coated with other materials as described herein, for binding to, or otherwise associating with, surfaces of the oral cavity to deliver actives and/or provide other benefits thereto.

Any of a variety of substrate particles and polymers or other coatings materials may be used in the present invention to provide the coated particles by coating the coating material onto the substrate particles. In certain embodiments, the substrate particles comprise materials having carboxyl groups on the surface which can be used to react with amino groups on coating materials/polymers to form covalent bonds. In other embodiments, the coated particles are formed by adsorbing coating materials to the substrate. Examples of suitable substrate particles include particles or nanoparticles made from poly(lactic-co-glycolic acid) ("PLGA"), poly(lactic acid) ("PLA"), poly(cyanoacrylates) ("PACA"), poly(acrylic acid), poly(anhydrides), poly(amides), poly(ortho esters), poly(arginateene glycol), poly(ethylene glycol), poly(vinyl alcohol), poly(isobutylcyanoacrylate) ("PIBCA"), poly(ethylene oxide) ("PEO"), poly(caprolactone) ("PCL"), cellulose, starch, chitosan, carrageenan, alginates, xantham gum, gellan gum, pectins, combinations of two or more thereof and the like. Certain commercially available particles include ISP Captivates™ encapsulates (available from Ashland), Nanospheres 100 Acide Ascobique (available from Biosil Technologies, Inc.)—metrical particles made from a porous polymer and bioadhesive, and the like.

The particles of the present invention may be of any suitable size. In certain embodiments, substrate particles of the present invention have a size of from about 1 micron to about 750 nm, including, from about 1 micron to about 100 nanometers, about 50 microns to about 10 nanometers, and from about 200 nanometers to about 750 nanometers.

According to certain embodiments, the coated particles comprise coated PLGA particles.

Examples of suitable materials and polymers for use in coating the substrates to form coated particles of the present invention include materials having an amino group such as: amino acids, including, but not limited to, Leucine, Valine, Tryptophan, Methionine, Arginine, combinations of two or more thereof, and the like; linear polysaccharide with an amino group or other moieties that facilitate strong interactions between nano-particulate materials and oral surfaces (the mucosal surfaces or pellicle coated enamel/dentin). Typically, these moieties would include functionalities that enable ionic interactions and/or hydrogen bonding. As the tooth surface possesses a net negative charge, positively charged moieties and compounds have a strong interaction with the surface. Examples of such materials include, but are not limited to, chitosan, xantham gum, combinations of two or more thereof, and the like; polyvinyl pyrrolidone (PVP) and derivatives thereof (e.g. Plasdone K29/32 and Plasdone S-630 polymer available commercially from Ashland, USA), Cetylpyridinium chloride, Chlorhexidine, PVM/MA Copolymers and Isopropyl, ethyl, or butyl ester of PVM/MA Copolymers such as Gantrez, e.g. Gantrez S, S97, ES245, AN, MS, Gafquats such as Gafquats 440, 755N, HS-100, and HSi (free forming cationic polymers) and other polyquaterniums such as 7, 22, and 37, Allantoin, Aqualon, Blanose, and Bondwell (sodium carboxymethylcellulose (CMC)), Wavemax (*Linum Usitatissimum* (Linseed) Seed Extract (and) *Salvia Hispanica* Seed Extract (combination of polysacharrides from Linseed and Chia seed-bioadhesive property), UV adhesives or urethane methacylate used in dental composites (Genomer 4297, CQ, 4205, 4256), Dextrans, Dextrins (maltodextrin, cellodextrin, Icodexttrin, pyrodextrins, cyclodextrins etc.), Merquats and other polyquaterniums (Lubrizol) such as 5, 7SPR, 100, 550PR, and S, Polyquaternium 6, Polyquaternium 10 w 1.5-2.2% Nitrogen, Polyquaternium 10 w 0.8-1.1% Nitrogen, Tetrahydropyrimidines (oxantel, morantel, carbantel, febantel, and pyrantel), poly(styrene sulfonic acid) ("PSSA"), methyl methacrylate, diethylaminoethyl methacrylate and combinations thereof (e.g. Kollicoat Smart Seal 30D); Distearmonium/Diethonium Chloride PG Dimethicone (e.g. Silquat JR 4B); Dimethicone PEG-8 Phosphate (e.g. Siliphos A 100); mixtures of two or more of the above, and the like; and compounds described by the Formula I:

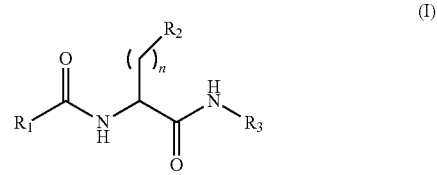

(I)

wherein:
R$_1$ is a linear or branched, saturated or unsaturated aliphatic group having from 5 to 22 carbon atoms;
R$_2$ is selected from the group consisting of the free base and corresponding salt forms of the functional groups:
—NH$_2$,

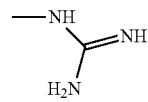

said salt versions having an anion X$^-$ preferably selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate;
n is from 0 to 4; and
R$_3$ is a linear or branched, saturated or unsaturated aliphatic group having from 1 to 6 carbon atoms.

The compositions of Formula I may have any suitable linear or branched, saturated or unsaturated aliphatic group having from 5 to 22 carbons for R$_1$. Examples of suitable linear or branched, saturated or unsaturated aliphatic groups having from 5 to 22 carbons include, C$_5$ to C$_{22}$ linear or branched alkyl groups, such as, pentyl, hexyl, heptyl, octyl, nonyl, decyl, undecyl, dodecyl, up to docosanyl, and the like; as well as, $C_5$ to $C_{22}$ linear or branched alkylene groups such as myristolyl up to docasanhexayl, and the like.

In certain embodiments, $R_1$ is linear or branched alkyl group having a carbon chain of from 5 to 22 carbons atoms, including for example, pentyl, hexyl, heptyl, octyl, nonyl, decyl, undecyl, dodecyl up to docasonyl. In certain other embodiments, $R_1$ is linear or branched alkyl group having a carbon chain of from 7 to 18 carbons atoms, including for example, heptyl, octyl, nonyl, decyl, undecyl, dodecyl, tridecyl, tetradecyl, pentadecyl, hexadecyl, heptadecyl and octadecyl. In still other embodiments, $R_1$ is linear or branched alkyl group having a carbon chain of from 9 to 14 carbons atoms, including for example, decyl, undecyl, dodecyl up to tetradecyl. In certain embodiments, $R_1$ is an undecyl group. In certain embodiments, $R_1$ is a heptyl group. In certain embodiments, $R_1$ is a heptadecyl group.

In certain embodiments, $R_1$ is linear or branched alkenyl group having a carbon chain of from 5 to 22 carbons atoms, including for example, 9-hexadecenyl, 9-octadecenyl, 11-decenyl, 9,12-octadecandienyl, 9,12,15-octadecatrienyl, 6,9,12-octadecatrienyl, 9-eicosenyl, 5,8,11,14-eicosatetraenyl, 13-docosenyl and 4,7,10,13,16,19-docosaheaenyl. In certain other embodiments, $R_1$ is linear or branched alkenyl group having a carbon chain of from 16 to 20 carbons atoms, including for example, 9-hexadecenyl, 9-octadecenyl, 11-decenyl, 9,12-octadecandienyl, 9,12,15-octadecatrienyl, and 6,9,12-octadecatrienyl.

In certain embodiments, $R_1$ is a branched alkyl group having a carbon chain of from 5 to 22 carbons atoms, including for example, 2-decyldodecanyl, 2-nonyltridecanyl, 2-octyltetradecanyl, 2-heptylpentadecanyl, 2-hexylhexadecanyl, 2-pentylheptadecanyl, 21-methylicosanyl, 18-ethylicosanyl, 16-propylnonadecyl, and 14-butyloctadecyl.

The compositions of Formula I may comprise an $R_2$ group that is an amine group in its free base form ($-NH_2$) or a salt thereof, or a guanidinyl functional group in its free base form ($-NH(CNH)NH_2$) or a salt thereof. Examples of suitable amine salts and guanidinyl salts include salts of such groups having an anion (X–) selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain embodiments, the composition of the present invention has an $R_2$ group that is an amine group in its free base form ($-NH_2$). In certain other embodiments, the composition of the present invention has an $R_2$ group that is a guanidinyl group in its free base form ($-NH(CNH)NH_2$). In certain embodiments, the composition of the present invention has an $R_2$ group that is an amine salt having an anion selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain other embodiments, the $R_2$ amine salt has an anion selected from the group consisting of acetate, benzoate, bromide, chloride, citrate, fumarate, gluconate, iodide, fluoride, lactate, malate, nitrate, oxalate, phosphate, sulfate, and in certain other embodiments an anion selected from the group consisting of bromide, chloride, iodide, fluoride, oxalate, and phosphate. In addition, in certain embodiments, the composition of the present invention has an $R_2$ group that is a guanidinyl salt having an anion selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain other embodiments, the $R_2$ guanidinyl salt has an anion selected from the group consisting of acetate, benzoate, bromide, chloride, citrate, fumarate, gluconate, iodide, fluoride, lactate, malate, nitrate, oxalate, phosphate, sulfate, and in certain other embodiments an anion selected from the group consisting of bromide, chloride, iodide, fluoride, oxalate, and phosphate.

The compositions of Formula I may have any suitable linear or branched, saturated or unsaturated aliphatic group having from 1 to 6 carbons for $R_3$. Examples of suitable linear or branched, saturated or unsaturated aliphatic groups having from 1 to 6 carbons include, $C_1$ to $C_6$ linear or branched alkyl groups, such as, methyl, ethyl, propyl, isopropyl, butyl, isobutyl, sec-butyl, tert-butyl, pentyl, tert-pentyl, neopentyl, isopentyl, hexyl, isohexyl, neohexyl; as well as, $C_2$ to $C_6$ linear or branched alkenyl groups such as vinyl, allyl, propenyl, butenyl, pentenyl, hexenyl, and the like. In certain embodiments, $R_3$ is linear or branched alkyl group having a carbon chain of from 1 to 4 carbons atoms, including for example, methyl, ethyl, propyl, isopropyl, butyl, sec-butyl, isobutyl, and tert-butyl. In certain other embodiments, $R_3$ is linear or branched alkyl group having a carbon chain of from 1 to 3 carbons atoms, including for example, methyl, ethyl, propyl and isopropyl. In certain embodiments, $R_3$ is an ethyl group.

In certain embodiments, $R_3$ is linear or branched alkenyl group having a carbon chain of from 2 to 6 carbons atoms, including for example, vinyl, allyl, propenyl, butenyl, pentenyl, hexenyl, and the like as well as mixture thereof. In certain other embodiments, $R_3$ is linear or branched alkylene group having a carbon chain of from 2 to 4 carbons atoms, including for example, vinyl, allyl, propenyl, and butenyl.

In the compounds of Formula I, n can be from zero to four. In certain embodiments, n is from 1 to 4, in certain embodiments from 2 to 4, in certain embodiments 3 to 4. In certain particular embodiments, n is 0. In certain other embodiments n is 1, in other embodiments n is 2, in other embodiments n is 3 and in other embodiments n is 4.

According to certain embodiments of the invention, the compounds of Formula I are compounds wherein $R_2$ is a guanidinyl functional group in its free base form ($-NH(CNH)NH_2$) or a salt thereof; n is 3 or 4, preferably 3; $R_3$ is an aliphatic group having a carbon chain of about 2 carbons atoms, for example an ethyl group; and $R_1$ is a linear or branched, saturated or unsaturated aliphatic group, including for example an alkyl group, having from 9 to 16 carbon atoms, including from about 10 to about 16 carbon atoms, about 10 to about 15 carbon atoms, about 10 to about 14 carbon atoms, about 10 to about 13 carbon atoms, about 11 to about 14 carbon atoms, about 11 to about 15 carbon atoms, about 11 to about 16 carbon atoms, and about 11, and/or about 13 carbon atoms.

In certain other embodiments, the compounds of Formula I are compounds wherein $R_2$ is a guanidinyl functional group in its free base form ($-NH(CNH)NH_2$) or a salt thereof; n is 3; $R_1$ is a linear or branched, saturated or unsaturated aliphatic group, including for example an alkyl group, having about 11 carbon atoms; and $R_3$ is a linear or branched, saturated or unsaturated aliphatic group, including for example an alkyl group, having a carbon chain length of about 1 to 11 carbons atoms, including from about 2 to about 10 carbon atoms, about 2 to about 9 carbon atoms, about 2 to about 8 carbon atoms, about 3 to about 11 carbon atoms, about 3 to about 10 carbon atoms, about 3 to about 9 carbon atoms, about 3 to about 8 carbon atoms, and about 2, about 6, and/or about 8 carbon atoms.

In certain other embodiments, the compounds of Formula I are compounds wherein $R_2$ is a guanidinyl functional group in its free base form (—NH(CNH)NH$_2$) or a salt thereof; n is 3; $R_1$ is a linear or branched, saturated or unsaturated aliphatic group, including for example an alkyl group, having about 7 carbon atoms; and $R_3$ is a linear or branched, saturated or unsaturated aliphatic group, including for example an alkyl group, having a carbon chain length of about 7 to 16 carbons atoms, including from about 7 to about 15 carbon atoms, about 7 to about 14 carbon atoms, about 7 to about 13 carbon atoms, about 7 to about 12 carbon atoms, about 7 to about 11 carbon atoms, and about 7, and/or about 11 carbon atoms.

In certain other embodiments, the compounds of Formula I are compounds wherein $R_2$ is an amine group in its free base form (—NH$_2$) or a salt thereof; and n is 1, 3, or 4. Examples of such compounds include those wherein n is 3; $R_1$ is a linear or branched, saturated or unsaturated aliphatic group, including for example an alkyl group, having about 7 carbon atoms; and $R_3$ is a linear or branched, saturated or unsaturated aliphatic group, including for example an alkyl group, having a carbon chain length of about 1 to 11 carbons atoms, including from about 2 to about 10 carbon atoms, about 2 to about 9 carbon atoms, about 2 to about 8 carbon atoms, about 3 to about 11 carbon atoms, about 3 to about 10 carbon atoms, about 3 to about 9 carbon atoms, about 3 to about 8 carbon atoms, and about 8, and/or about 11 carbon atoms. Other examples include compounds wherein n is 3; $R_1$ is a linear or branched, saturated or unsaturated aliphatic group, including for example an alkyl group, having about 11 carbon atoms; and $R_3$ is a linear or branched, saturated or unsaturated aliphatic group, including for example an alkyl group, having a carbon chain length of about 1 to 11 carbons atoms, including from about 1 to about 10 carbon atoms, about 1 to about 9 carbon atoms, about 1 to about 8 carbon atoms, about 1 to about 7 carbon atoms, about 1 to about 6 carbon atoms, about 2 to about 11 carbon atoms, about 2 to about 10 carbon atoms, about 2 to about 9 carbon atoms, about 2 to about 8 carbon atoms, about 2 to about 7 carbon atoms, about 2 to about 6 carbon atoms, and about 2 and/or about 6 carbon atoms.

One example of a compound of Formula I of the present invention is [amino({[4-dodecanamido-4-(ethylcarbamoyl)butyl]amino})methylidene]azanium (compound 9) as shown below.

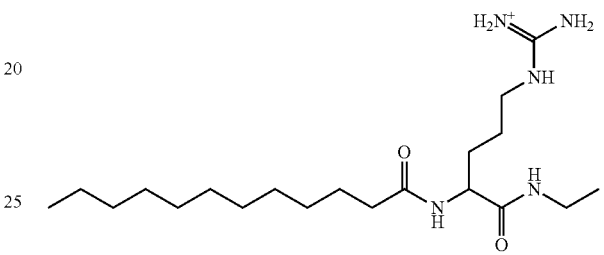

As shown in the formula above, compound 9 represents a compound of Formula I wherein $R_1$ is an undecyl group, $R_2$ is a guanidinyl group in its free base form, $R_3$ is an ethyl group, and n is 3.

Other examples of compounds of the present invention include, but are not limited to compounds described by the formulae:

Compound 5

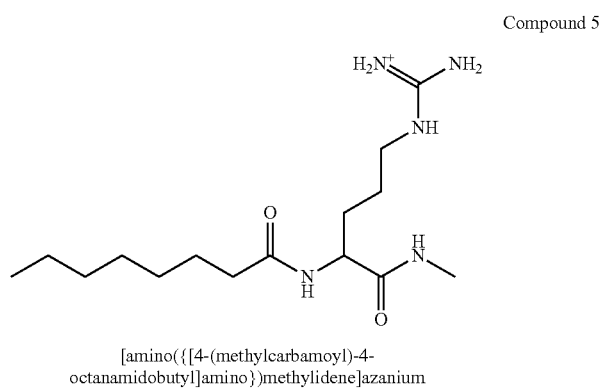

[amino({[4-(methylcarbamoyl)-4-octanamidobutyl]amino})methylidene]azanium

Compound 8

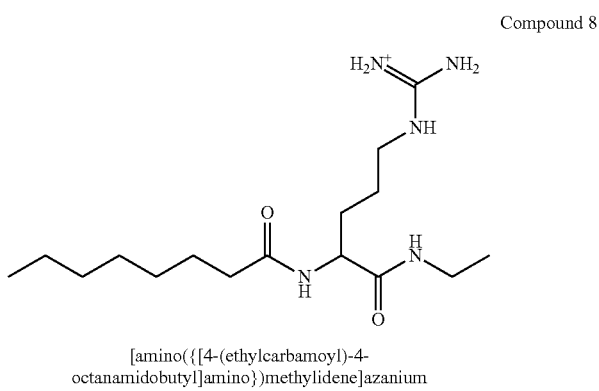

[amino({[4-(ethylcarbamoyl)-4-octanamidobutyl]amino})methylidene]azanium

Compound 11

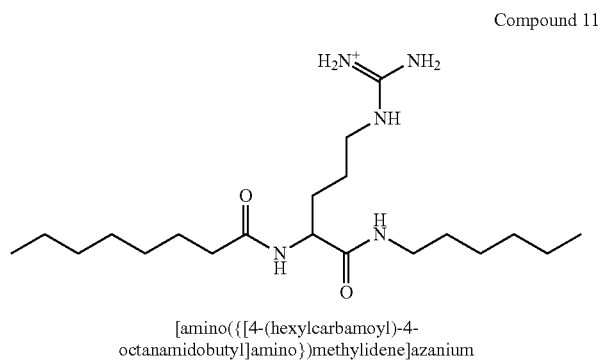

[amino({[4-(hexylcarbamoyl)-4-octanamidobutyl]amino})methylidene]azanium

Compound 6

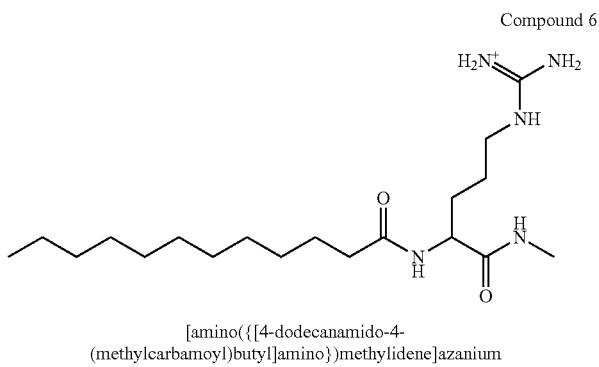

[amino({[4-dodecanamido-4-(methylcarbamoyl)butyl]amino})methylidene]azanium

-continued
Compound 12
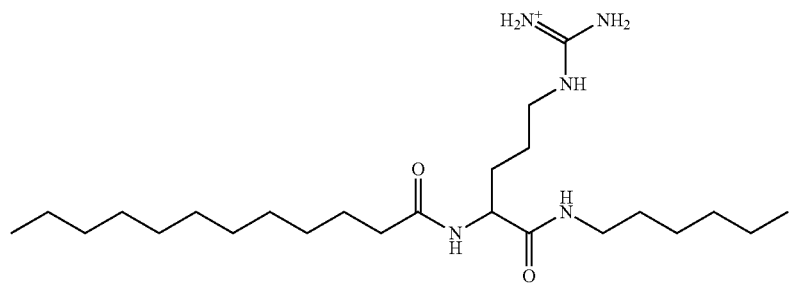
[amino({[4-dodecanamido-4-(hexylcarbamoyl)butyl]amino})methylidene]azanium
Compound 7
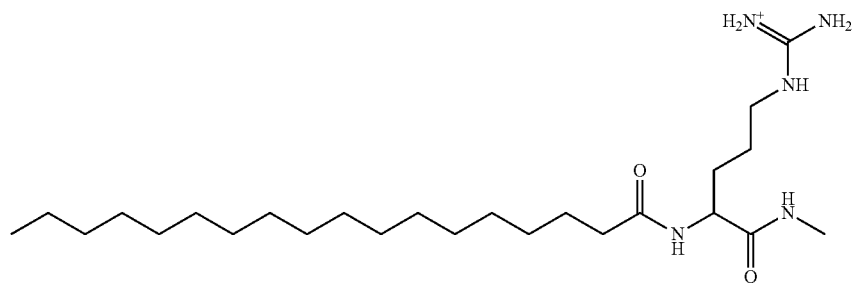
[amino({[4-(methylcarbamoyl)-4-octadecanamidobutyl]amino})methylidene]azanium
Compound 10
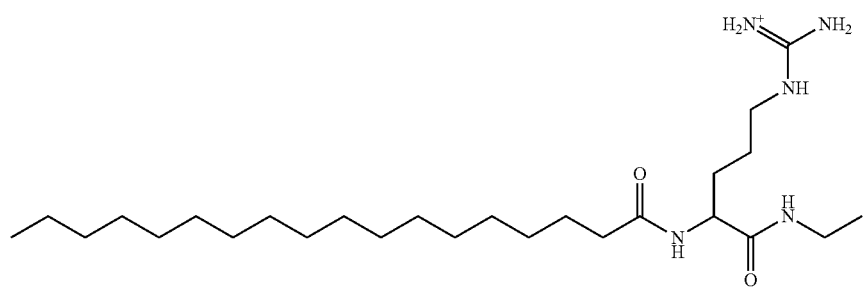
[amino({[4-(ethylcarbamoyl)-4-octadecanamidobutyl]amino})methylidene]azanium
Compound 13
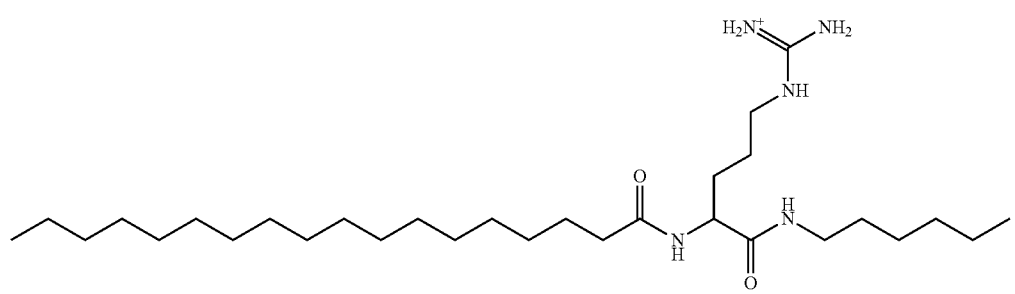
[amino({[4-(hexylcarbamoyl)-4-octadecanamidobutyl]amino})methylidene]azanium -continued Compound 4

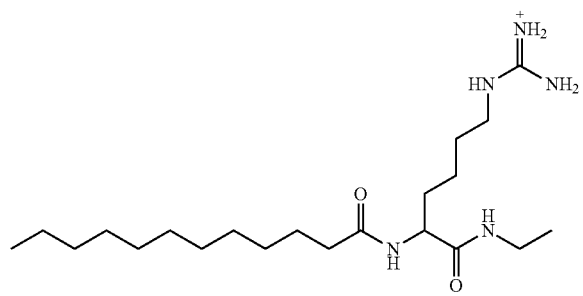

[amino({[5-dodecanamido-5-(ethylcarbamoyl)pentyl]amino})methylidene]azanium

Compound 3

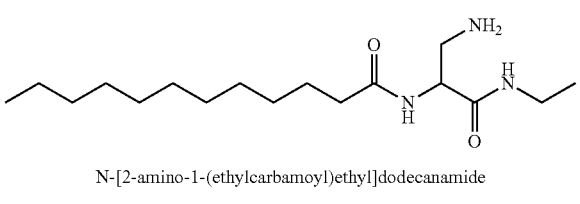

N-[5-amino-1-(ethylcarbamoyl)pentyl]dodecanamide

Compound 1

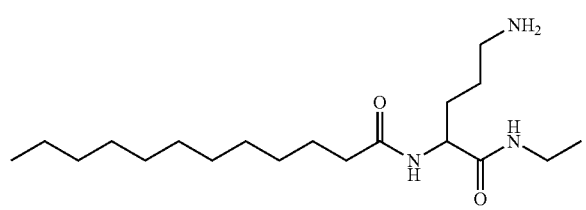

N-[4-amino-1-(ethylcarbamoyl)butyl]dodecanamide

Compound 2

N-[2-amino-1-(ethylcarbamoyl)ethyl]dodecanamide

Compound 14

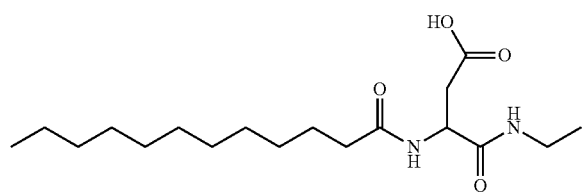

3-dodecanamido-4-(ethylamino)-4-oxobutanoic acid

Compound 15

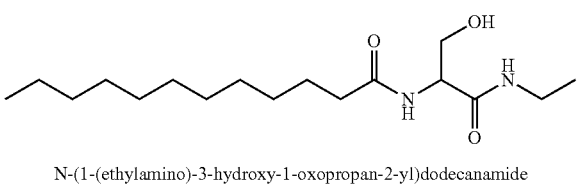

N-(1-(ethylamino)-3-hydroxy-1-oxopropan-2-yl)dodecanamide

Compound 16

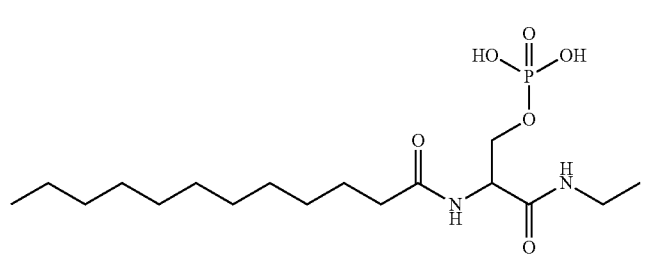

2-dodecanamido-3-(ethylamino)-3-oxopropyl dihydrogen phosphate

Compound 17

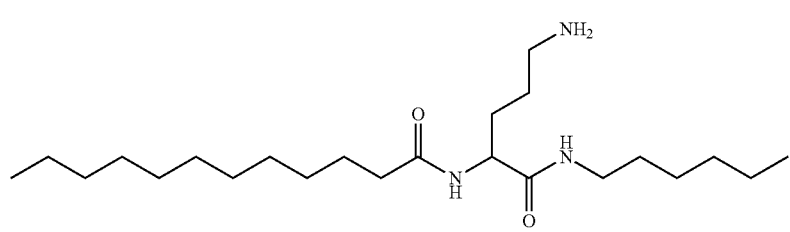

N-(5-amino-1-(hexylamino)-1-oxopentan-2-yl)dodecanamide

-continued

Compound 18
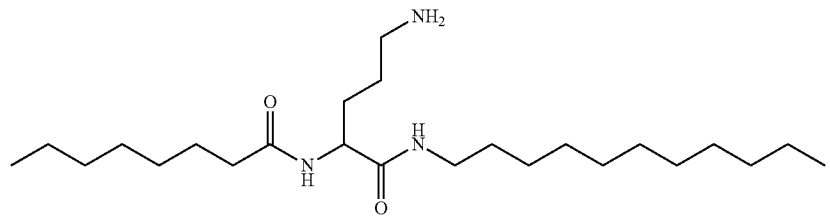
N-(5-amino-1-oxo-1-(undecylamino)pentan-2-yl)octanamide

Compound 19
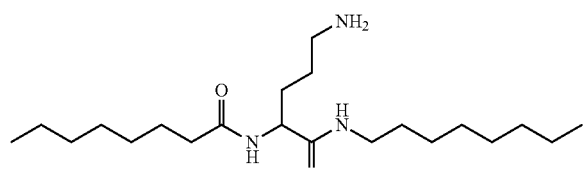
N-(5-amino-1-(octylamino)-1-oxopentan-2-yl)octanamide

Compound 20
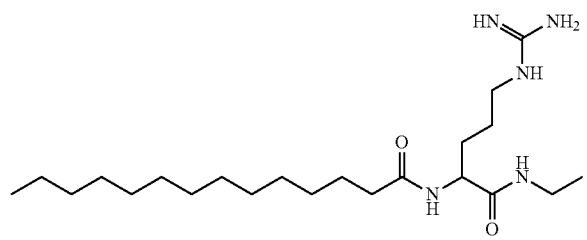
N-(1-(ethylamino)-5-guanidino-1-oxopentan-2-yl)tetradecanamide Compound 21
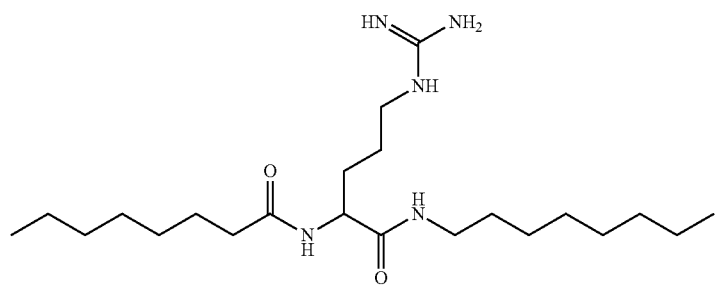
N-(5-guanidino-1-(octylamino)-1-oxopentan-2-yl)octanamide Compound 22
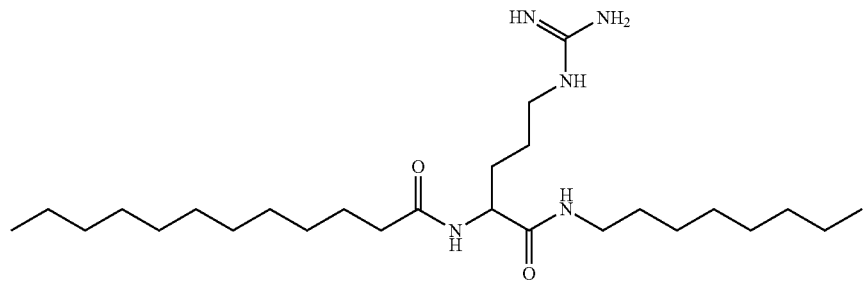
N-(5-guanidino-1-(octylamino)-1-oxopentan-2-yl)dodecanamide Compound 23
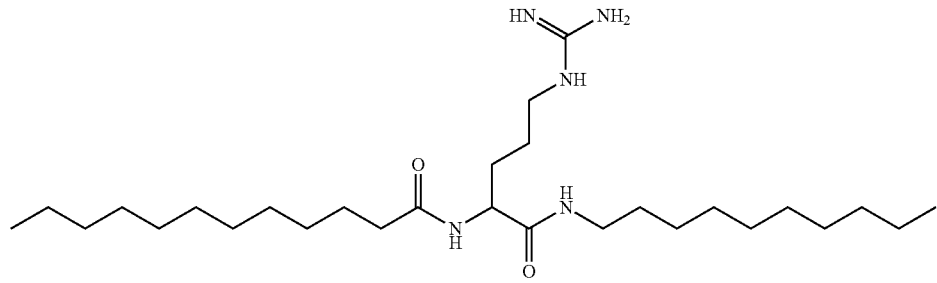
N-(1-(decylamino)-5-guanidino-1-oxopentan-2-yl)dodecanamide -continued

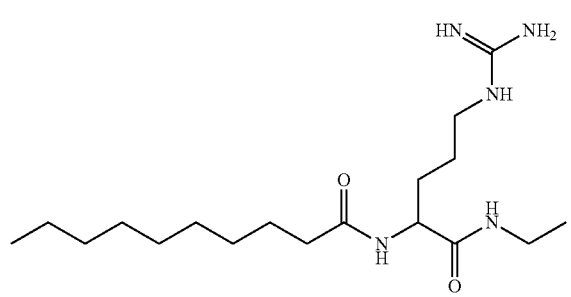

N-(1-(ethylamino)-5-guanidino-1-oxopentan-2-yl)decanamide

Compound 24

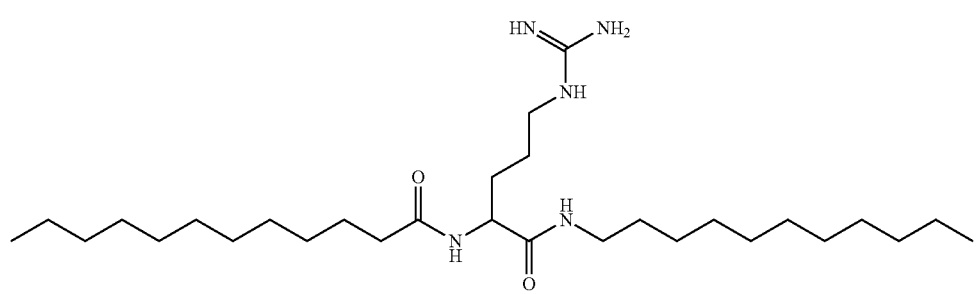

N-(5-guanidino-1-oxo-1-(undecylamino)pentan-2-yl)dodecanamide

Compound 25

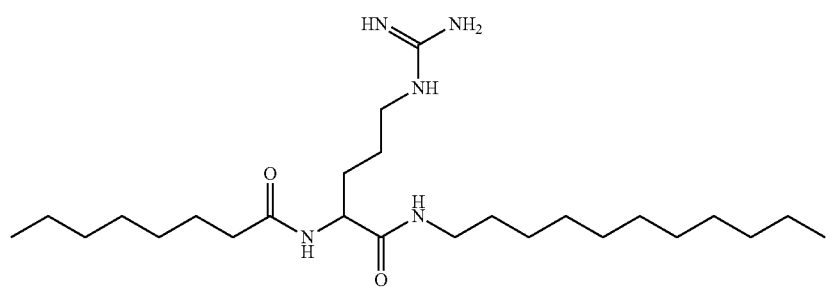

N-(5-guanidino-1-oxo-1-(undecylamino)pentan-2-yl)octanamide

Compound 26

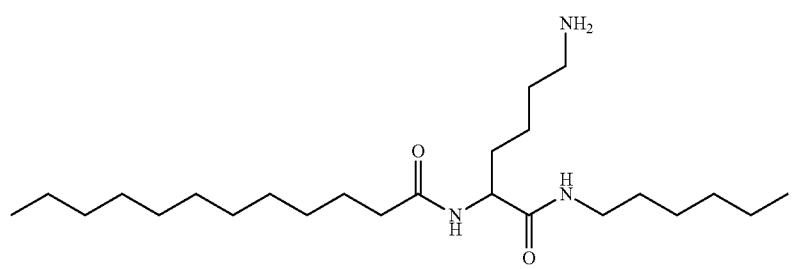

Compound 31

Other examples of suitable materials for use as coatings herein include phospholipid surfactant compounds such as cocamidopropyl PG-dimonium chloride phosphate; myristamidopropyl PG-dimonium chloride phosphate; lauramidopropyl PG-dimonium chloride phosphate and mixtures thereof. In certain embodiments, the phospholipid surfactant is selected from the group consisting of cocamidopropyl PG-dimonium chloride phosphate; myristamidopropyl PG-dimonium chloride phosphate and mixtures thereof. In certain embodiments the phospholipid surfactant is myristamidopropyl PG-dimonium chloride phosphate. A variety of such materials are available commercial from Croda under the trade name Arlasilk™.

In certain embodiments, the particles of the present invention may comprise any of a variety of active materials for providing a healthcare benefit. Examples of suitable actives include actives for use in the oral cavity including, but are not limited to, any of a variety of actives for providing benefits such as mouth cleaning, including debris removal, antimicrobial, including anti-plaque, anti-gingivitis, and reduction in malodor, biofilm disruption, prevention of bacterial attachment, modification of oral microbial community structure, modification of the metabolic profile of oral microbes, antiviral activity, anti-inflammatory, pH balance, tooth whitening, stain prevention, anti-sensitivity, anti-caries, enamel strengthening, breath freshening, oral hydration/dry mouth relief, erosion repair and prevention, active delivery and retention, sensory enhancement, mouth feel alteration, pain relief, wound healing, and the like.

In certain embodiments, compositions of the present invention comprise essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, avender oil, mustard oil, phenol, phenyl salicylate, pine oil, pine needle oil, sassafras oil, spike lavender oil, storax, thyme oil, tolu balsam, turpentine oil, clove oil, and combinations thereof.

In certain preferred embodiments, the present invention comprises one or more bioactive essential oils selected from the group consisting of menthol, thymol, eucalyptol, and methyl salicylate. In certain preferred embodiments, the invention comprises menthol and at least one other essential oil selected from thymol, eucalyptol, and methyl salicylate. In certain preferred embodiments, the invention comprises menthol and eucalyptol, menthol, eucalyptol and thymol, or menthol, eucalyptol, thymol, and methyl salicylate. Thymol, $[(CH_3)_2CHC_6H_3(CH_3)OH]$, also known as isopropyl-m-cresol], is only slightly soluble in water but is soluble in alcohol, and its presence is one of the reasons alcohol was necessary in the well-established, high alcohol commercial mouth rinses. Methyl salicylate, $[C_6H_4OHCOOCH_3$, also known as wintergreen oil], additionally provides flavoring to the together with its antimicrobial function. Eucalyptol ($C_{10}H_{18}O$, also known as cineol) is a terpene ether and provides a cooling, spicy taste. Eucalyptol may be used in place of thymol in certain formulations in the same amount if desired. Menthol ($CH_3C_6H_9(C_3H_7)OH$), also known as hexahydrothymol) is also only slightly soluble in alcohol, and is fairly volatile. Menthol, in addition to any antiseptic properties, provides a cooling, tingling sensation.

Other suitable antimicrobial agents include Halogenated Diphenyl Ethers, 2',4,4'-trichloro-2-hydroxy-diphenyl ether (Triclosan), 2,2'-dihydroxy-5,5'-dibromo-diphenyl ether, Halogenated Salicylanilides, 4'5-dibromosalicylanilide, 3,4', 5-trichlorosalcylanilide, 3,4',5-tribromosalicylanilide, 2,3,3', 5-tetrachlorosalicylanilide, 3,3',5-tetrachlorosalicylanilide, 3,5, dibromo-3'-trifluoromethyl salicylanilide, 5-n-octanoyl-3'-trifluoromethyl salicylanilide, 3,5-dibromo-4'-trifluoromethyl salicylanilide, 3,5-dibromo-3'-trifluoro methyl salicylanilide (Flurophene), Benzoic Esters, Methyl-p-Hydroxybenzoic Ester, Ethyl-p-Hydroxybenzoic Ester, Propyl-p-Hydroxybenzoic Ester, Butyl-p-Hydroxybenzoic Ester, Halogenated Carbanilides, 3,4,4'-trichlorocarbanilide, 3-trifluoromethyl-4,4'-dichlorocarbanilide 3,3',4-trichlorocarbanilide, Phenolic Compounds (including phenol and its homologs, mono- and poly-alkyl and aromatic halo (e.g. F, Cl, Br, I)-phenols, resorcinol and catechol and their derivatives and bisphenolic compounds), 2 Methyl-Phenol, 3 Methyl-Phenol, 4 Methyl-Phenol, 4 Ethyl-Phenol, 2,4-Dimethyl-Phenol, 2,5-Dimethyl-Phenol, 3,4-Dimethyl-Phenol, 2,6-Dimethyl-Phenol, 4-n-Propyl-Phenol, 4-n-Butyl-Phenol, 4-n-Amyl-Phenol, 4-tert-Amyl-Phenol, 4-n-Hexyl-Phenol, 4-n-Heptyl-Phenol, 2-Methoxy-4-(2-Propenyl)-Phenol (Eugenol), Mono-And Poly-Alkyl And Aralkyl Halophenols, Methyl-p-Chlorophenol, Ethyl-p-Chlorophenol, n-Propyl-p-Chlorophenol, n-Butyl-p-Chlorophenol, n-Amyl-p-Chlorophenol, sec-Amyl-p-Chlorophenol, n-Hexyl-p-Chlorophenol, Cyclohexyl-p-Chlorophenol, n-Heptyl-p-Chlorophenol, n-Octyl-p-Chlorophenol, O-Chlorophenol, Methyl-o-Chlorophenol, Ethyl-o-Chlorophenol, n-Propyl-o-Chlorophenol, n-Butyl-o-Chlorophenol, n-Amyl-o-Chlorophenol, tert-Amyl-o-Chlorophenol, n-Hexyl-o-Chlorophenol, n-Heptyl-o-Chlorophenol, p-Chlorophenol, o-Benzyl-p-Chlorophenol, o-Benzyl-m-methyl-p-Chlorophenol, o-Benzyl-m,m-dimethyl-p-Chlorophenol, o-Phenylethyl-p-Chlorophenol, o-Phenylethyl-m-methyl-p-Chlorophenol, 3-Methyl-p-Chlorophenol, 3,5-Dimethyl-p-Chlorophenol, 6-Ethyl-3-methyl-p-Chlorophenol, 6-n-Propyl-3-methyl-p-Chlorophenol, 6-iso-Propyl-3-methyl-p-Chlorophenol, 2-Ethyl-3,5-dimethyl-p-Chlorophenol, 6-sec Butyl-3-methyl-p-Chlorophenol, 2-iso-Propyl-3,5-dimethyl-p-Chlorophenol, 6-Diethylmethyl-3-methyl-p-Chlorophenol, 6-iso-Propyl-2-ethyl-3-methyl-p-Chlorophenol, 2-sec Amyl-3,5-dimethyl-p-Chlorophenol, 2-Diethylmethyl-3,5-dimethyl-p-Chlorophenol, 6-sec Octyl-3-methyl-p-Chlorophenol, p-Bromophenol, Methyl-p-Bromophenol, Ethyl-p-Bromophenol, n-Propyl-p-Bromophenol, n-Butyl-p-Bromophenol, n-Amyl-p-Bromophenol, sec-Amyl-p-Bromophenol, n-Hexyl-p-Bromophenol, cyclohexyl-p-Bromophenol, o-Bromophenol, tert-Amyl-o-Bromophenol, n-Hexyl-o-Bromophenol, n-Propyl-m,m-Dimethyl-o-Bromophenol, 2-Phenyl Phenol, 4-chloro, 2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, 5-chloro-2-hydroxydiphenylemthane, Resorcinol And Its Derivatives, Resorcinol, Methyl-Resorcinol, Ethyl-Resorcinol, n-Propyl-Resorcinol, n-Butyl-Resorcinol, n-Amyl-Resorcinol, n-Hexyl-Resorcinol, n-Heptyl-Resorcinol, n-Octyl-Resorcinol, n-Nonyl-Resorcinol, Phenyl-Resorcinol, Benzyl-Resorcinol, Phenylethyl-Resorcinol, Phenylpropyl-Resorcinol, p-Chlorobenzyl-Resorcinol, 5-Chloro-2,4-Dihydroxydiphenyl Methane, 4'-Chloro-2,4-Dihydroxydiphenyl Methane, 5-Bromo-2,4-Dihydroxydiphenyl Methane, 4'-Bromo-2,4-Dihydroxydiphenyl Methane, Bisphenolic Compounds, Bisphenol A, 2,2'-methylene bis(4-chlorophenol), 2,2'-methylene bis(3,4,6-trichlorophenol) (hexachlorophene), 2,2'-methylene bis(4-chloro-6-bromophenol), bis(2-hydroxy-3,5-dichlorophenyl) sulfide, bis (2-hydroxy-5-chlorobenzyl) sulfide, menthoxy-1,2-propanediol, ortho-methoxy cinnamic aldehyde, menthyl-3-hydroxybutanoate, combinations of two or more thereof, and the like.

Other antimicrobial agents include, but are not limited to: hexetidine; fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid vitamin E, vitamin E acetate, apigenin and mixtures thereof; long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2- octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof); cyclic sesquiterpene alcohols, such as farnesol; N'-alkyl-L-arginine alkyl ester (e.g., Lauroyl Arginine Ethyl Ester) and salts such as described in U.S. Pat. No. 5,874,068 to Engelman et al., herein incorporated by reference in its entirety; Amino acid derivative compounds as described in U.S. Patent Publication No. 20160145203 to Gambogi, et al., herein incorporated by reference in its entirety; antimicrobial peptides, such as retrocyclin (RC101), protegrin-1 (PG1) or KSL-W; and surfactants, including cationic surfactants such as cetylpyridinium chloride, chlorhexedine and mixtures thereof. Additionally, antimicrobial extracts of certain botanical or fruits may be included, including proanthocyanidins (PACs) found in cranberry such as, flavan-3-ols (and polymers of), procyanidins (and polymers of), terpenes (and polymers of), hydroxybenzole acids, hydroxycinnamic acids, anthocyanidins (and polymers of), flavonols (and polymers of), and other cyanidins and peonidins. Oils such as peppermint oil and sage oil are also useful herein.

Other suitable actives include fluoride ion sources such as sodium fluoride, sodium monofluorophosphate, stannous fluoride, and amine fluorides (providing, for example, about 1-5000 ppm of fluoride ion, optionally about 200-1150 ppm of fluoride ion); non-fluoride tooth strengthening agents such as calcium carbonate, alpha tricalcium phosphate, or phosphoryl oligosaccharides of calcium, anticalculus agents, such as water-soluble pyrophosphate salts, preferably alkali metal pyrophosphates, polyacrylates and copolymers of maleic anhydride or acid and methyl vinyl ether (e.g., Gantrez), as described, for example, in U.S. Pat. No. 4,627,977, to Gaffar et al.; as well as, e.g., polyamino propane sulfonic acid (AMPS), zinc citrate trihydrate, polypeptides (such as polyaspartic and polyglutamic acids), and mixtures of two or more thereof; anti-calculus agents such as water-soluble pyrophosphate salts, preferably alkali metal pyrophosphates; chelating agents such as tartaric acid and pharmaceutically-acceptable salts thereof, citric acid and alkali metal citrates and mixtures thereof; tooth desensitization agents which reduce tooth sensitivity including potassium salts such as potassium nitrate and potassium chloride and strontium salts such as strontium chloride and strontium acetate; tooth whitening agents and vitamins such as vitamin A; as well as pigments and colorants such as inorganic white pigments, inorganic colored pigments, pearling agents, filler powders and the like, as well as talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures of two or more thereof.

Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to antimicrobial properties.

Ingredients which are metabolized by oral bacteria to cause a benefit effect in the oral cavity may also be included in these materials, including arginine, arginine monohydrochloride, and inulin-type fructans, maltodextrin, fructooligosaccharides and galactooligosaccharides. Additionally, the invention may be used to deliver probiotic strains of bacteria, including certain species of lactobacilli and bifidobacteria, *Saccharomyces* spp, streptococci, enterococci and commensal *Escherichia coli*.

The invention may also be used to deliver pharmaceutical actives to treat oral diseases or disease symptoms which occur in the oral cavity or the oropharynx, such as anesthetics, antibiotics, antifungals, antiviral, and anti-inflammatory compounds.

Methods of Making

Any suitable means for making the coated particles of the present invention may be used. In certain embodiments, the methods comprise reacting the coating materials/polymers with the substrate materials under conditions sufficient to covalently bond the materials/polymers to the surface of the substrate materials. In other embodiments, the methods comprise adsorbing the coating material onto the substrate. Examples of general methods of making coated PLGA particles as non-limiting examples of the present invention are provided below. Other substrate particles of the present invention may also be used in place of PLGA in the method.

Surface Conjugation

PLGA particles contain carboxyl groups on the surface which can be used to react with amino groups on biologic compounds to form covalent bonds. The following conjugation protocol serves as a generalized guideline for conjugating biomolecules (coating materials) to PLGA particles.

1. Suspend PLGA particles in 50 mM MES buffer (pH 5.2) (Company, Product Code) via vortexing. Sonicate if necessary.
2. Prepare a 200 mg/ml N-(3-Dimethylaminopropyl)-N'-ethylcarbodiimide hydrochloride EDC (Sigma Aldrich Prod. E1769) solution in 50 µl 50 mM MES buffer (pH 5.2); Use immediately.
3. Add the EDC solution to the microsphere suspension.
4. Mix gently end-over-end.
5. Add biomolecule equivalent to 200-500 µg. Mix gently end-over-end or briefly vortex.
6. Incubate for 2-4 hours at room temperature with gentle mixing.
7. Centrifuge mixture for 10 minutes at an appropriate G force. Note: Actual G forces needed to pelletize the particles depend on the particle size. Save this supernatant for determination of the amount of bound biomolecule.
8. Resuspend microsphere pellet in 10 mM Tris buffer containing 0.05% BSA (pH 8.0).
9. Repeat Steps 7-8 and combine supernatants for use in bound biomolecule calculation.
10. Store conjugated microspheres at 4° C. in Tris storage buffer.

EDC has been used in peptide synthesis; crosslinking proteins to nucleic acids; and preparation of immunoconjugates as examples. EDC is generally utilized as a carboxyl activating agent for amide bonding with primary amines. In addition, it will react with phosphate groups.

Adsorption

1. Suspend 50 mg PLGA particle in 1 ml water to produce 5% by weight, PLGA particle mixture.

2. Add PLGA particle mixture that is an equivalent of 2.5 mg of PLGA (i.e. 50 μL) particle in 500 μl of technology solution, mix gently end over end for 30 minutes at room temperature.
3. centrifuge at 1500 G for 20 minutes.

Methods of Use

Applicants have recognized that the coated particles of the present invention may be used to introduce actives to, or otherwise to prevent, treat or provide benefits to, surfaces of the oral cavity. In particular, the particles may be introduced into the oral cavity to adhere to one or more surfaces therein to introduce actives and/or provide benefits to the oral cavity.

The particles of the present invention may comprise any of a variety of active materials for providing a benefit to the oral cavity. According to certain embodiments, the methods of the present invention comprise introducing a coated particle of the present invention into the oral cavity to provide one or more benefits selected from the group consisting of: disrupting a biofilm on a surface of the oral cavity, reducing bacterial attachment to a surface of the oral cavity, removing biofilm from a surface, inhibiting plaque and plaque formation, reducing gingival inflammation, gingival swelling and redness, reduction in bleeding, and prevention of gingivitis.

Any suitable surface of the oral cavity may be contacting in accord with the methods of the present invention including one or more surfaces selected from the group consisting of surfaces of one or more teeth, surfaces of the gums, combinations of two or more thereof, and the like. In certain preferred embodiments, the coated particles are used to contact a tooth surface.

In each of the above methods, the composition of the claimed method may be introduced to the surface to be contacted via any of a variety of methods. In certain embodiments, the composition is introduced into the oral cavity and applied to the surface by a user as a mouthwash or mouth rinse. In certain embodiments, the composition is introduced to the oral cavity and applied to the surface as a toothpaste on an article for cleaning the teeth, e.g. a toothbrush. The compositions of the present invention may be further introduced via the mouth and applied to the surface as a gum, lozenge, dissolvable strip, or the like.

Furthermore, the contacting step of the methods of the present invention may comprise contacting the surface with the composition for any suitable amount of time. In certain embodiments, the contacting step comprises contacting the surface for less than thirty seconds. In certain embodiments, the contacting step comprises contacting the surface with the composition for thirty seconds or more, for example, for about thirty seconds, for about forty seconds, for about one minute, or for greater than one minute.

Assays

Applicants have developed new assays to determine the viability for coated materials to stick to surfaces of the oral cavity, in particular, hydroxyapatite surfaces (surfaces of the tooth). According to certain embodiments, the assay comprises coating hydroxyapatite particles (HAP) with saliva, mixing the saliva-coated HAP with polymer coated PLGA particles to be tested and incubating, washing the resulting HAP with test coated PLGA particles to remove loose polymer-test PLGA particles and collecting the eluent, and measuring the collected eluent to determine fluorescence. Via these methods the fluorescence of the eluent can be used to determine how much coated particle is sticking to the HAP and how much has eluted off. In particular, the particle binding assays provides a measure of the interactions that occur between polymer coated PLGA particles and the saliva coated HAP, such as polymer-pellicle bindings, as well as the degree of affinity (weak, strong, or no connection) for which the reactants bind together.

An example procedure according to one embodiment using PLGA particles is provided below.

Fluorescent PLGA Particle Binding Assay Procedure:
1. Weigh out x mg of HAP particles (enough for 10 mg per sample well, i.e. if 10 sample wells 100 mg of HAP).
2. Add artificial saliva to the particles at a concentration of 100 uL per 10 mg and incubate for 15-minutes at 37° C.
3. Transfer HAP particle/saliva suspension into 3.0 um filter plate by adding 100 uL of the suspension to each respective well. Be sure to use single channel pipet and swirl suspension before pipetting the suspension.
4. Remove the saliva from the wells of the filter plate by vacuum filtration. Be sure to use the adhesive tape to cover the wells as the vacuum is not strong enough to remove any liquid without such. NOTE: it may take a few cycles of covering the plate with tape, removing it and re-covering it.
5. Add polymer coated particles to each well and incubate at 37° C. for 10 minutes while shaking (do not over incubate).
6. Remove treatment by repeating step 4. NOTE: Collect the eluent.
7. Wash any loosely bound polymer coated fluorescent PLGA particles off the HAP particles with 200 uL of water. NOTE: Collect the eluent.
8. Repeat step 7 as many times until you can no longer detect fluorescence. NOTE: Collect the eluent each time. Monitor the effluent and make note of the color (after all three washes the final eluent should appear to be a clear solution).
9. Add all eluents from steps 6-8 into a 96-well opaque or black bottom plate.
10. Read fluorescence in opaque or black 96-well plate. Excitation/emission: 460/500 nm.

Another embodiment is provided below:

Fluorescent PLGA Particle Adsorption Assay

Procedure:
1. Weigh out x mg of HAP particles (x=enough for 10 mg per sample well, i.e. if 10 sample wells 100 mg of HAP will be weighed out).
2. Add artificial saliva to the particles at a concentration of 100 uL per 10 mg and incubate for 30-minutes to 24 hours at 37° C. with continuous shaking.
3. After incubation, transfer HAP particle/saliva suspension into 3.0 um filter plate by adding 100 uL of the suspension to each respective well. Be sure to use single channel pipet and swirl suspension before pipetting the suspension.
4. Remove the saliva from the wells of the filter plate by vacuum filtration. Be sure to use the aluminum foil to cover the wells as the vacuum is not strong enough to remove any liquid without such. NOTE: it may take a few cycles of covering the plate with foil, removing it and re-covering it.
5. Adsorption:
   i. Suspend 50 mg PLGA particle in 1 ml water to produce 5% by weight, PLGA particle mixture.
   ii. Add PLGA particle mixture that is an equivalent of 2.5 mg of PLGA (i.e. 50 μL) particle in 500 μL of technology solution, mix gently end over end for 30 minutes at room temperature.
   iii. Centrifuge at 1500 G for 20 minutes.

6. Carefully remove the supernatant using pipet without disturbing the pellet formed
7. After isolating the pellet, add XX µL of DI water to the tube. Resuspend the pellet in water by mixing using vortex. (XX=120 uL multiplied by number of wells for each technology). This solution will be used to measure total fluorescence of the technology.
8. Add polymer coated particles to each well and incubate at 37° C. for 10 minutes while shaking (do not over incubate).

TABLE 1

|  | CONTROL | LAE | HLA | HMP | PSSA |
|---|---|---|---|---|---|
| elute 1 | 44004 | 53131 | 51145 | 46139 | 45424 |
| elute 2 | 44258 | 55917 | 55056 | 47294 | 46104 |
| wash 1 | 44989 | 54437 | 48126 | 46326 | 46941 |
| wash 2 | 19323 | 19844 | 29424 | 16783 | 22667 |
| wash 3 | 6163 | 9800 | 12342 | 6276 | 7785 |
| wash 4 | 4102 | 6124 | 8299 | 3732 | 3111 |

TABLE 2

|  | Cont. H20 1 | HLA 2 | 17 3 | 18 4 | 31 5 | Leucine 6 | Valine 7 | Tryptophan 8 | Methionine 9 | Arginine 10 | K29 11 | Chitosan 12 | Iron 13 | Xanthan Gum 14 |
|---|---|---|---|---|---|---|---|---|---|---|---|---|---|---|
| elute 1 | 40179 | 40940 | 46331 | 45981 | 470777 | 44022 | 43637 | 42969 | 43874 | 43544 | 42235 | 41487 | 37783 | 38275 |
| elute 2 | 41602 | 39325 | 44069 | not elute | not elute | 43775 | 39421 | 41819 | 42047 | 43597 | 42833 | 44100 | not elute | 40309 |
| wash 1 | 33717 | 40128 | 40072 | not elute | not elute | 36404 | 37812 | 38450 | 38765 | 42145 | 38568 | 42579 | not elute | 42501 |
| wash 2 | 10541 | 20092 | 1670 | not elute | not elute | 15709 | 19342 | 17180 | 15714 | 17362 | 15563 | 32460 | not elute | 35681 |
| wash 3 | 3023 | 8046 | 5902 | 50511 | 51951 | 5150 | 4276 | 4255 | 3525 | 4069 | 4930 | 26204 | 42823 | 6160 |
| wash 4 | 1490 | 4353 | 3129 | 33023 | 36129 | 2540 | 2594 | 2047 | 1858 | 2129 | 2494 | 19569 | 26957 | 24156 |
| wash 5 | 1329 | 2945 | 1734 | 19396 | 17702 | 1612 | 1795 | 1338 | 1292 | 1448 | 1519 | 12608 | 9313 | 33728 |

9. Remove treatment by repeating step 4. NOTE: Collect the eluent.
10. Wash any loosely bound polymer coated fluorescent PLGA particles off the HAP particles with 100 uL of DI water. NOTE: Collect the eluent.
11. Repeat step 10 as many times until you can no longer detect fluorescence. NOTE: Collect the eluent each time. Monitor the effluent and make note of the color (after all three washes the final eluent should appear to be a clear solution).
12. Add 75 uL of each eluent and total fluorescence solution from steps 7-11 into a 96-well opaque or black bottom plate.
13. Read fluorescence using Tecan infinite M200, in opaque or black clear bottom 96-well plate. Excitation/Emission: 460/500 nm, Gain: 50

Note:

For 13871-10 incubation of HAP particles in artificial saliva (Step 2) was 24 hours.

For 13871-12 incubation of HAP particles in artificial saliva (Step 2) was 2 hours.

EXAMPLES

Example 1

Applicants have made several coated particles in accord with the Surface Conjugation procedure of present invention as described herein. As shown in Tables 1-2, applicants have coated PLGA particles with Leucine, Valine, Tryptophan, Methionine, and Arginine with Chitosan and Xanthan gum, with polyvinyl pyrrolidone (Plasdone K29/32), ethyl lauroyl arginate HCl (LAE and with several compounds of Formula I. Such coated particles were then assayed in accord with the Fluorescent PLGA Particle Binding Assay Procedure described herein and the results shown in the Tables 1 and 2 below.

The results in the tables show the degree of for each polymer-coated PLGA particle with the saliva coated HAP. The polymers that generated a very strong binding were chitosan and xanthan gum. The strong binders were LAE, HLA, and compounds 17, 18, and 31. The medium binders were all the amino acids and PVP. The weak binder was PSSA and the molecules that exhibited no interaction were iron and HMP.

Example 2

Applicants have made and tested several coated particles in accord with the Fluorescent PLGA Particle Adsorption Assay of present invention as described herein using the materials as shown in the tables. As shown in the Tables applicants have coated particles with Distearmonium/Diethonium Chloride PG Dimethicone (Silquat J2 4B), chitosan (Chitosan LMW), polyquaternium-10 (Ucare JR 30 M, Ucare LR-400), myristamidopropyl PG-dimonium chloride phosphate (Arlaskil PTM-LQ-AP), Dimethicone PEG-8 Phosphate (Siliphos A-100), and methyl methacrylate (MMA) and diethylaminoethyl methacrylate (DEAEMA) (Kollicoat Smart Seal 30D).

Calculation:

The raw data from the fluorescent reader was used for calculation. The mean of readings of total fluorescence of each technology was calculated to obtain average total fluorescence. The data from collected eluents and washes was normalized using average total fluorescence of respective resuspended PLGA particles and technology. This was calculated for each sample well for all washes treated with various technologies. The formula used for normalization is:

(Raw data point of fluorescence of eluent from wash of a technology sample well/Average total fluorescence of that technology)*100

The average and standard deviation was calculated for each wash step of respective technology. The graph plotted shows normalized fluorescence per technology with error bars showing standard of deviation of normalized data.

TABLE 3

|  |  | 1% Silquat JR-4B | Water | 0.25% Chitosan LMW | 0.25% Ucare JR 30 M | 0.25% Ucare LR 400 | Ariasilk PTM-LQ-AP | Siliphos A 100 | Kollicoat Smart Seal 30D |
|---|---|---|---|---|---|---|---|---|---|
| Total florescence | 1 | 4603 | 4255 | 4664 | 2405 | 3535 | 4647 | 4357 | 7020 |
|  | 2 | 4936 | 4746 | 5116 | 4789 | 3281 | 4877 | 4547 | 7662 |
|  | Average | 4769.5 | 4500.5 | 4890 | 3597 | 3408 | 4762 | 4452 | 7341 |

TABLE 4

|  |  | 1% Silquat JR-4B | Water | 0.25% Chitosin LMW | 0.25% Ucare JR 30 M | 0.25% Ucare LR 400 | Arlasilk PTM-LQ-AP | Siliphos A 100 | Kollicoat Smart Seal 30D |
|---|---|---|---|---|---|---|---|---|---|
| Raw data | Treatment elute | 1251 | 2523 | 2855 | 8 | 90 | 943 | 3231 | 29 |
|  |  | 1277 | 2498 | 2876 | 8 | 87 | 1002 | 3293 | 35 |
|  |  | 1303 | 2676 | 2928 | 5 | 38 | 1049 | 2974 | 30 |
|  | Wash 1 | 363 | 1513 | 1724 | 4 | 217 | 654 | 1893 | 5 |
|  |  | 364 | 1551 | 1888 | 4 | 203 | 496 | 1819 | 5 |
|  |  | 361 | 1562 | 2055 | 3 | 93 | 531 | 1856 | 6 |
|  | Wash 2 | 61 | 181 | 176 | 4 | 118 | 170 | 216 | 3 |
|  |  | 49 | 154 | 210 | 1 | 127 | 55 | 130 | 3 |
|  |  | 47 | 143 | 156 | 2 | 68 | 195 | 101 | 2 |
|  | Wash 3 | 43 | 114 | 128 | 2 | 93 | 88 | 32 | 1 |
|  |  | 30 | 145 | 83 | 3 | 81 | 32 | 29 | 2 |
|  |  | 32 | 147 | 83 | 3 | 29 | 67 | 27 | 1 |

TABLE 5

Total Fluorescence

|  | 1% PQ6 | 0.5% PQ6 | 0.25% PQ6 | 0.25% Ucare LR400 | 0.125% Ucare LR400 | Water | 0.25% Ucare JR 400 | 0.125% Ucare JR 400 | 1% Kollicoat smartseal 30 D | 0.5% Kollicoat smartseal 30 D | 0.25% Kollicoat smartseal 30 D |
|---|---|---|---|---|---|---|---|---|---|---|---|
| 1 | 3258 | 3617 | 3837 | 3967 | 2966 | 3805 | 2091 | 3850 | 6352 | 8996 | 7048 |
| 2 | 3653 | 3545 | 3867 | 4072 | 3047 | 3885 | 2217 | 3829 | 6502 | 8339 | 7140 |
| avg | 3455.5 | 3581 | 3852 | 4019.5 | 3006.5 | 3845 | 2154 | 3839.5 | 6427 | 8667.5 | 7094 |

TABLE 6

Raw Data

|  | 1% PQ6 | 0.5% PQ6 | 0.25% PQ6 | 0.25% Ucare LR400 | 0.125% Ucare LR400 | Water | 0.25% Ucare JR 400 | 0.125% Ucare JR 400 | 1% Kollicoat smartseal 30 D | 0.5% Kollicoat smartseal 30 D | 0.25% Kollicoat smartseal 30 D |
|---|---|---|---|---|---|---|---|---|---|---|---|
| Waste | 1688 | 1411 | 1308 | 866 | 200 | 2680 | 260 | 1315 | 4 | 4 | 23 |
|  | 1699 | 1266 | 1123 | 748 | 272 | 2515 | 420 | 1357 | 3 | 3 | 19 |
|  | 1748 | 1128 | 1183 | 757 | 345 | 2663 | 372 | 1334 | 3 | 6 | 19 |
| Wash 1 | 844 | 652 | 768 | 1111 | 58 | 1495 | 101 | 1543 | 2 | 2 | 10 |
|  | 901 | 889 | 910 | 1211 | 62 | 1403 | 153 | 1718 | 2 | 1 | 21 |
|  | 918 | 808 | 953 | 1063 | 81 | 1521 | 130 | 1536 | 3 | 2 | 21 |
| Wash 2 | 163 | 199 | 287 | 430 | 3 | 102 | 2 | 263 | 1 | 2 | 9 |
|  | 155 | 214 | 346 | 481 | 4 | 147 | 2 | 323 | 2 | 1 | 6 |
|  | 135 | 245 | 354 | 509 | 3 | 126 | 2 | 416 | 1 | 1 | 10 |
| Wash 3 | 56 | 83 | 129 | 284 | 3 | 38 | 2 | 174 | 1 | 1 | 5 |
|  | 56 | 111 | 199 | 329 | 3 | 41 | 1 | 180 | 2 | 2 | 4 |
|  | 67 | 121 | 172 | 344 | 4 | 43 | 1 | 211 | 2 | 1 | 9 |

The results show the degree of affinity for each technology-coated PLGA particle with the saliva coated HAP. The polymers that generated very strong to strong binding (0-10% and 10-25% fluorescence in wash elutes) were polyquaternium 10 (such as UCare LR 400, UCare JR 30, UCare JR 400), co-polymer consisting of co-polymer comprising methyl methacrylate (MMA) and diethylaminoethyl methacrylate (DEAEMA) (such as Kollicoat Smart seal 30 D). The polymers that generated medium binding (25-40% fluorescence in wash elutes) are polyquaternium 6 (such as Tilamar Quat 640), Myristamidopropyl PG-Dimonium Chloride Phosphate (such as Arlasilk PTM), silicones (such as Distearmonium/Diethonium Chloride PG Dimethicone, Silquat J2 4B). The molecules that showed weak binding to no binding (40%<fluorescence in wash elutes) are water, chitosan with low molecular weight, anionic molecules (such as Siliphos A 100).

Retention Calculation: The percentage of retention was calculated by assuming total percentage to be 100%. The percent normalized elutes from treatment and washes where then subtracted from 100% of total fluorescence to measure degree of affinity (percent of retention) for each technology-coated PLGA particle with saliva coated HAP.

The results show the degree of affinity for each technology-coated PLGA particle with saliva coated HAP. The polymers that showed very strong to strong retention were (90-100% and 75-90%) were polyquaternium 10 (such as UCare LR 400, UCare JR 30, UCare JR 400), co-polymer consisting of co-polymer comprising methyl methacrylate (MMA) and diethylaminoethyl methacrylate (DEAEMA) (such as Kollicoat Smart seal 30 D). The polymers that generated medium binding (60-75%) are polyquaternium 6 (such as Tilamar Quat 640), Myristamidopropyl PG-Dimonium Chloride Phosphate (such as Arlasilk PTM), silicones (such as Distearmonium/Diethonium Chloride PG Dimethicone, Silquat J2 4B). The molecules that showed weak binding to no binding (40-60% and 40%>) are water, chitosan with low molecular weight, anionic molecules (such as Siliphos A 100). This interaction is also shown in the photographs of the respective wells as indicated by the intensity of yellow-green color.

What is claimed is:

1. A coated particle which binds to, adheres or associates with the surfaces of the oral cavity, comprising:
    (a) a substrate which is a particle or nanoparticle made from poly(lactic-co-glycolic acid) ("PLGA"), and
    (b) a coating covalently bonded to the substrate which is ethyl lauroyl arginate HCl.

2. The particle according to claim 1 further comprising an active ingredient.

3. A method of providing a benefit to the oral cavity comprising introducing to said oral cavity a coated particle according to claim 1.

4. A method of providing a benefit to the oral cavity comprising introducing to said oral cavity a coated particle according to claim 2.

* * * * *